United States Patent [19]

Sun et al.

[11] Patent Number: 5,995,860
[45] Date of Patent: *Nov. 30, 1999

[54] IMPLANTABLE SENSOR AND SYSTEM FOR MEASUREMENT AND CONTROL OF BLOOD CONSTITUENT LEVELS

[75] Inventors: Xiaoguang Sun, King of Prussia; Jeffrey I. Joseph, Penn Valley, both of Pa.

[73] Assignee: Thomas Jefferson University, Philadelphia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/500,388

[22] Filed: Jul. 6, 1995

[51] Int. Cl.$^6$ .............................. A61B 5/00; A61M 5/142
[52] U.S. Cl. ......................... 600/341; 600/316; 600/322; 604/67; 604/891.1
[58] Field of Search ..................................... 128/633, 634; 604/50, 66, 67, 890.1, 891.1; 356/39; 600/322, 323, 310, 316, 326, 327, 339, 340, 341

[56] References Cited

U.S. PATENT DOCUMENTS

| | | | |
|---|---|---|---|
| 3,837,339 | 9/1974 | Aisenbert et al. | 128/213 |
| 4,013,074 | 3/1977 | Siposs . | |
| 4,073,292 | 2/1978 | Edelman | 128/214 |
| 4,398,908 | 8/1983 | Siposs . | |
| 4,435,173 | 3/1984 | Siposs et al. . | |
| 4,538,616 | 9/1985 | Rogoff | 128/632 |
| 4,621,643 | 11/1986 | New, Jr. et al. | 128/633 |
| 4,633,878 | 1/1987 | Bombardieri | 128/635 |
| 4,679,562 | 7/1987 | Luksha | 128/635 |
| 4,704,029 | 11/1987 | Van Heuvelen | 128/633 |

(List continued on next page.)

FOREIGN PATENT DOCUMENTS

| | | |
|---|---|---|
| 4-15046 | 1/1992 | Japan . |
| 92/11801 | 7/1992 | WIPO . |

OTHER PUBLICATIONS

Zeller, H., et al., Blood glucose measurement by infrared spectroscopy, *International Journal of Artificial Organs*, vol. 12, 129 (1989).

Arnold, M.A., et al., Determination of physiological levels of glucose in an aqueous matrix with digitally filtered Fourier Transformation Neat–Infrared Spectra, *Analytical Chemistry*, vol. 62, 1457 (1990).

Shichiri, M., et al., An artificial endocrine pancreas—problems awaiting solution for long term clinical applications of a glucose sensor, *Frontiers of Medical and Biological Engineering*, vol. 3, 283 (1991).

(List continued on next page.)

*Primary Examiner*—Jennifer Bahr
*Assistant Examiner*—Eric F. Winakur
*Attorney, Agent, or Firm*—Panitch Schwarze Jacobs & Nadel, P.C.

[57] ABSTRACT

An implantable device for sensing in vivo the level of at least one blood constituent in mammalian vascular tissue has at least one source of radiation from infrared through visible light, arranged to direct the radiation at the tissue where it is affected by interaction with the tissue, and a plurality of detectors. Each detector has associated with it a filter transparent to a discrete narrow band of radiation, and each detector provides an output signal representative of detected radiation in that narrow band. The detectors are located with respect to the tissue to receive radiation affected by the tissue. The invention also encompasses a device for measuring and controlling the level of a blood constituent, such as glucose, in a mammal, and includes an implantable infrared source and sensor module for directing infrared radiation through vascular tissue and for sensing the infrared radiation after it has passed through the tissue and generating an output signal representative of the sensed infrared radiation. The device includes a processor module responsive to the output signal from the infrared source and sensor module which performs spectral analysis of the output signal and derives from that analysis a control signal representative of the level of the blood constituent. The device further includes an insulin pump for dispensing doses of insulin in response to the control signal for blood glucose regulation.

20 Claims, 6 Drawing Sheets

U.S. PATENT DOCUMENTS

| | | | |
|---|---|---|---|
| 4,822,336 | 4/1989 | DiTraglia | 604/50 |
| 4,825,879 | 5/1989 | Tan et al. | 128/633 |
| 4,830,488 | 5/1989 | Heinze et al. | 356/41 |
| 4,865,038 | 9/1989 | Rich et al. | 128/633 |
| 4,890,621 | 1/1990 | Hakky | 128/635 |
| 4,979,509 | 12/1990 | Hakky | 128/635 |
| 5,054,487 | 10/1991 | Clarke | 128/633 |
| 5,101,814 | 4/1992 | Palti | 128/635 |
| 5,127,406 | 7/1992 | Yamaguchi | 128/633 |
| 5,179,951 | 1/1993 | Knudson | 128/633 |
| 5,190,041 | 3/1993 | Palti | 128/635 |
| 5,204,532 | 4/1993 | Rosenthal | 250/341 |
| 5,305,745 | 4/1994 | Zacouto | |
| 5,353,792 | 10/1994 | Lubbers et al. | 128/634 |
| 5,361,759 | 11/1994 | Genevier et al. | 128/634 |
| 5,368,028 | 11/1994 | Palti | 128/635 |
| 5,474,552 | 12/1995 | Palti | 604/67 |
| 5,598,841 | 2/1997 | Taniji et al. | |
| 4,807,629 | 2/1989 | Baudino et al. | 128/419 |

OTHER PUBLICATIONS

Henise, H.M., et al., Noninvasive blood glucose sensors based on near–infrared spectroscopy, *Artificial Organs*, vol. 18, 439 (1994).

Heise, H.M., et al., Multivariate Determination of Glucose in Whole Blood by Attenuated Total Reflection Infrared Spectroscopy, *Analytical Chemistry*, vol. 61 No. 18, Sep. 15, 1989.

Johnson, K. W., et al., In Vivo Evaluation of an Electroenzymatic Glucose Sensor Implanted in Subcutaneous Tissue, *Biosensors & Bioelectronics*, vol. 7, pp. 709–714, 1992.

Miyazawa, T., Characteristic Infrared Bands of Monosubstituted Amides, *The Journal of Chemical Physics*, vol. 24, No. 2, Feb. 1956.

Abe, T., et al., Characterization of Glucose Microsensors for Intracellular Measurements, *Anal. Chem. 1992*, vol. 64, pp. 2160–2163, 1992.

Conway, J., Ph.D., A New Approach for the Estimation of Body Composition: Infrared Interactance, *The American Journal of Clinical Nutrition 40*: Dec., 1984, pp. 1123–1130.

Abel, P., et al., The GOD–$H_2O_2$–Electrode as an Approach to Implantable Glucose Sensors. (no date available).

Lanza, E., Determination of Moisture, Protein, Fat, and Calories in Raw Port and Beef by Near Infrared Spectroscopy.

Tallagrand, T., et al., Evaluation of Implantable Glucose Enzyme–Based Sensors with Extracorporeal Blood Shunt, 1988. (best copy available).

Mathlouthi, M., Laser–Raman Spectra of D–Glucose and Sucrose in Aqueous Solution, *Carbohydrate Research*, vol. 81, (1980) pp. 203–212.

Gough, D. A., Issues Related to In Vitro Operation of Potentially Implantable Enzyme Electrode Glucose Sensors. (no date avaiable).

Stewart, R., et al., Infrared Analysis of Serum Protein from One Hundreds and Five Hundred Adults, *J. Lab. & Clin. Med.* Sep. 1960, vol.56, No. 3.

Clark, L. C., et al., Long–Term Stability of Electroenzymatic Glucose Sensors Implanted in Mice, *Trans Am Soc Artif Intern Organs*, vol. 34, 1988.

Arnold, M., et al., Determination of Physiological Levels of Glucose in an Aqueous Matrix with Digitally Filtered Fourier Transform Near–Infrared Spectra, *Analytical Chemistry*, 1990, vol. 62, pp. 1457–1464.

Ertefai, S., et al., Physiological Preparation for Studying the Response of Subcutaneously Implanted Glucose and Oxygen Sensors, Biomed Engineering, vol. 11, Sep. 1989.

Marbach, R., et al., On the Efficiency of Algorithms for Multivariate Linear Calibration used in Analytical Spectroscopy, *Trends in Analytical Chemistry*, vol. 11, No. 8, 1992.

Chang, K., et al., Validation and Bioengineering Aspects of an Impantable Glucose Sensor. (no date available).

Heise, H.M., et al., Multivariate Determination of Blood Substrates in Human Plasma, *International Conference on Fourier Transform Spectroscopy* (1991).

Pickup, J. C., et al., Progress Towards In Vivo Glucose Sensing with a Ferrocene–Mediated Amperometric Enzyme Electrode. (no date available).

Bauer, B., et al., Monitoring of Glucose in Biological Fluids by Fourier–Transform Infrared Spectrometry with a Cylindrical Internal Reflectance Cell, *Analytical Chimica Acta*, (1987).

Guyton, J.R., et al., The Development of an Implantable electrochemical Glucose Sensor: Response to Glucose in Bovine Serum Ultrafiltrate. (no date available).

Haaland, D., et al., Reagentless Near–Infrared Determination of Glucose in Whole Blood Using Multivariate Calibration, *Applied Spectroscopy*, vol. 46, No. 10, 1992.

Cammann K. Implantable Electrochemical Glucose Sensors—State of the Art. (no date available).

Hopkinson, J., et al., Applications of Attenuated Total Reflection in the Infrared Analysis of Carbohydrates and Biological Whole Cell Samples in Aqueous Solution, *Analyst*, vol. 112, Apr. 1987.

Xie, S., Ph.D., et al., Performances of Potentially Implantable. Rechargeable Glucose Sensors In Vitro at Body Temperature, *Biomedical Instrumentation & Technology*, Sep./Oct. 1991.

Kaiser, N., Communications, *Transaction on Biomedical Engineering*, vol. BME–26, No. 10, Oct. 1979.

Wilson, G., et al., Progress toward the Development of an Implantable Sensor for Glucose, *Clinical Chemistry*, vol. 38, No. 9, 1992.

Guyton, A., M.D., Insulin, Glucagon, and Diabetes Mellitus, *Textbook of Medical Physiology*, 8th Edition.

Moatti–Sirat, D., et al., Towards Continuous Glucose Monitoring In Vivo Evaluation of a Miniaturized Glucose Sensor Implanted for Several Days in Rat Subcutaneous Tissue, *Diabetology*, vol. 35, pp. 224–230, 1992.

Velho, G., et al., Strategies for Calibrating a Subcutaneous Glucose Sensor, *Biomed. Biochimica Acta* (1989).

Armour, J. C., et al., Application of Chronic Intravascular Blood Glucose Sensor in Dogs, *Diabetes*, Dec. 1990.

Velho, G., et al., Determination of Peritoneal Glucose Kinetics in Rats: Implications for the Peritoneal Implantation of Closed–Loop Insulin Delivery Systems, *Diabetologia* (1989) vol. 32, pp. 331–336.

von Woedtke, T., et al., Implantable Glucose Sensors: Comparison between In Vitro and In Vivo 24 Kinetics, *The International Journal or Artificial Organs*, vol. 14, No. 8, pp. 473–481, 1991.

Kolendorf, K., et al., Determination of 24–Hour Insulin Infusion Pattern by an Artificial Endocrine Pancreas for Intravenous Insulin Infusion with a Miniature Pump, *Horm. Metab. Res.* vol. 13, pp. 245–249 (1981).

Poitout, V., et al., In Vitro and In Vivo Evaluation in Dogs of a Miniaturized Glucose Sensor. (no date available).

Goetz, F., Conference on Beta Cell Function, Transplantation, and Implantable Glucose Sensors: A Summary, *Metabolism*, vol. 23, No. 9, Sep., 1974.

Hollander, P.M.D., et al. Diabetes in Pregnancy, *Park Nicollet Medical Center*.

Fischer, U. et al., A Membrane Combination for Implantable Glucose Sensors. Measurement in Undiluted Biological Fluids, *Trans Am Soc Artif Intern Organs*, vol. 28, 1982.

Robinson, R. M., et al., Noninvasive Glucose Monitoring in Diabetic Patients: A Preliminary Evaluation, *Clinical Chemistry*, vol. 38, No. 9, 1992.

Woedtke, et al., In Situ Calibration of Implanted Electrochemical Glucose Sensors, *Biomed Biochim Acta*, vol. 48, 1989.

Schultz, J. S., et al., Affinity Sensor: A New Technique for Developing Implantable Sensors for Glucose and Other Metabolites, *Diabetes Care*, vol. 5, No. 3, May–Jun. 1982.

Xie, S., Performances of Potentially Implantable Rechargeable Glucose Sensors in Vito at Body Temperature, *Biomedical Instrumentation & Technology*, pp. 393–399.

Pickup, J. C., et al., Potentially–Implantable, Amperometric Glucose Sensors with Medical Electron Transfer: Improving the Operating Stability, *Biosensors* (1989).

Clark, L.C., Long–Term Implantation of Voltammetric Oxidase/Peroxide Glucose Sensors in the Rat Peritoneum, *Methods in Enzymology*, vol. 137.

Drake, R. F., et al., In Vitro and In Vivo Testing of an Electrocatalytic Glucose Sensor, *Electrocatalytic Glucose Sensor*.

Fisher, et al., Experience with an Implantable Glucose Sensor as a Prerequisite of an Artificial Beta Cell, *Biomed Biochim Acta*, vol. 43, 1984.

Lerner, H., et al., Measurement of Glucose Concentration in the Presence of Coreactants with a Platinum Electrode, *Diabetes Care*, vol. 5, No. 3 May–Jun. 1982.

Kondo, et al., Trial of new Vessel Access Type Glucose Sensor for Implantable Artificial Pancreas In Vivo, *Trans Am Soc Artif Intern Organ*, vol. 27, 1981.

Gilligan, B., J. MS, DVM, et al., Evaluation of a Subcutaneous Glucose Sensor out to Three Months in a Dog Model, *Diabetes Care*, vol. 17, No. 8, Aug. 1994.

Velho, G. et al., In Vitro and In Vivo Stability of Electrode Potentials in Needle–Type Glucose Sensors, *Diabetes*, vol. 38, Feb. 1989.

Armour, Jon C., et al., Application of Chronic Intravascular Blood Glucose Sensor in Dogs, *Diabetes Care*, vol. 39, Dec. 1990.

Fischer, U., et al., Wick Technique: Reference Method for Implanted Glucose Sensors, *Artificial Organs*, vol. 13, No. 15, 1989.

Hashiguchi, Y., M.D., et al., Development of a Miniaturized Glucose Monitoring System by Combining a Needle–Type Glucose Sensor With Microdialysis Sampling Method, *Diabetes Care*, vol. 17, No. 5, May 1994.

Preidel, W., et al., In Vivo Experiment with the Electrocatytic Glucose Sensor in Sheep, *Biosensors & Bioelectronics*, vol. 8 pp. 299–306, 1993.

Moussy, F., et al., Performance of Subcutaneously Implanted Needle–Type Glucose Sensors Employing a Novel Trilayer Coating, *Analytical Chemistry*, vol. 65, pp. 2072–2077, 1993.

Shichiri, M., et al., In Vivo Characteristics of Needle–Type Glucose Sensor–Measurement of Subcutaneous Glucose Concentrations in Human Volunteers. (no date available).

Poitout, V. et al., A Glucose Monitoring System for on Line Estimation in Man of Blood Glucose Concentration Using a Miniaturized Glucose Sensor Implanted in the Subcutaneous Tissue and a Wearable Control Unit, *Diabetologia*, vol. 36, pp. 658–663, 1993.

Meyerhoff, C., et al., Use of the Microdialysis Technique in the Monitoring of Subcutaneous Tissue Glucose Concentration, *The International Journal of Artificial Organs*, vol. 16, No. 5. 1993.

Sternberg, R., et al., Study and Development of Multilayer Needle–Type Enzyme based Glucose Microsensors, *Biosensors*, vol. 4, pp. 27–40, 1988.

Shichiri, M., et al., Wearable Artificial Endocrine Pancreas with Needle–Type Glucose Sensor, *The Lancet*, Nov. 20, 1982.

Shaw, G. W., et al., In Vitro Testing of a Simply constructed, Highly Stable Glucose Sensor Suitable for Implantation in diabetic Patients, *Biosensors & Bioelectronics*, vol. 6, pp. 401–406, 1991.

Clark, L. C. Jr., et al., Implanted Electroenzymatic Glucose Sensors, *Diabetes Care*, vol. 5, No. 3, May–Jun. 1982.

Pickup, J., et al., Implantable Glucose Sensors: Choosing the Appropriate Sensing Strategy, *Biosensors*, vol. 3, pp. 335–346, 1987.

Fischer, et al., Oxygen Tension at the Subcutaneous Implantation Site of Glucose Sensors, *Biochem. Biochim Acta*, vol. 48, pp. 965–971, 1989.

Kondo, T., et al., A Miniature Glucose Sensor, Implantable in the Blood Stream, *Diabetes Care*, vol. 5, No. 3, May–Jun. 1982.

Rebrin, K. et al., Subcutaneous Glucose Monitoring by Means of Electrochemical Sensors: Fiction or Reality?, *Journal of Biomedical Engineering*, vol. 14, Jan. 1992.

McKean, B., et al., A Telemetry–Instrumentation System for Chronically Implanted Glucose and Oxygen Sensors, *IEEE Transactions of Biomedical Engineering*, vol. 35, No. 7, Jul. 1988.

Claremont, D.J., et al., Subcutaneous Implantation of a Ferrocene–Mediated glucose sensor in Pigs, *Dabetologia*, vol. 29, pp. 817–821, 1986.

C. Meyerhoff, et al., Use of the Microdialysis Technique in the Monitoring of Subcutaneous Tissue Glucose Concentration, *The International Journal of Artificial Organs*, vol. 16, No. 5, pp. 268–275, 1993.

Fischer et al., "Assessment of subcutaneous glucose concentration: validation of the wick technique as a reference for implanted electrochemical sensors in normal and diabetic dogs", Diabetologia, vol. 30, pp. 940–945, 1987.

Pickup, J.C. et al., "In vivo molecular sensing in diabetes mellitus: an implantable glucose sensor with direct electron transfer", Diabetologia, vol. 32, pp. 213–217, 1989.

Rebrin, A., et al., Automated Feedback Control of Subcutaneous Glucose Concentraction in Diabetic Dogs, *Diabetologia*, vol. 32, pp. 573–576, 1989.

Koudelka, M., et al., In–Vivo Behaviour of Hypodermically Implanted Microfabricated Glucose Sensors, *Biosensors & Bioelectronics*, vol. 6, pp. 31–36, 1991.

FIG. 12

IMPLANTABLE SENSOR AND SYSTEM FOR MEASUREMENT AND CONTROL OF BLOOD CONSTITUENT LEVELS

FIELD OF THE INVENTION

The present invention relates to medical devices for sensing the level of a constituent in a body fluid, including but not limited to blood glucose, blood fatty acid, and blood amino acid levels. The present invention also relates to control of blood constituent levels in response to sensed levels to provide continuous monitoring and control of blood constituent levels to permit aggressive insulin therapy and concomitant clinical benefit of such therapy.

BACKGROUND OF THE INVENTION

Glucose is an important nutrient. During periods of moderate to heavy exercise, the muscles utilize large amounts of glucose to release energy. In addition, large amounts of glucose are taken up by muscle cells in the few hours after a meal. This glucose is stored in the form of muscle glycogen, and can later be used by the muscles for short periods of extreme use and to provide spurts or anaerobic energy for a few minutes at a time. Moreover, glucose is an essential nutrient for brain and spinal cord function. Glucose is the only nutrient that can normally be utilized by the brain, retina, and germinal epithelium of the gonads in sufficient quantity to supply those organs with their required energy. Brain tissue has an obligate requirement for a steady supply of blood glucose. When blood glucose levels fall below 50 mg/dl, memory loss, agitation, confusion, irritability, sweating, tachycardia, and hypertension commonly occur. Brain failure occurs when blood glucose levels fall below 30 mg/dl, and is associated with coma, hypoventilation, and vascular instability. Death may occur. Therefore, it is important to maintain the blood glucose concentration at a high enough level to provide this necessary nutrition.

At the same time, however, it is also important that the blood glucose concentration not rise too high. Glucose exerts a large osmotic pressure in the extracellular fluid. If glucose concentration rises to excessive levels, this can draw water out of the cells and cause considerable cellular dehydration. Excessively high blood glucose levels causes loss of glucose in the urine. This produces an osmotic diuresis by the kidneys, which can deplete the body of fluids and electrolytes.

The steady supply of blood glucose is tightly controlled by the pancreas and the liver. Following a meal, gastric digestion and intestinal absorption provide an increasing amount of carbohydrates, free fatty acids, and amino acids into the portal venous blood. Sixty percent of the glucose absorbed after a meal is immediately stored in the liver in the form of glycogen. Between meals, when the glucose concentration begins to fall, liver glycogen is dephosphorolated, allowing large quantities of glucose to diffuse out of the liver cells and into the blood stream. The liver, a large organ, can store six percent of its mass as glycogen. In contrast, muscle tissue can store only two percent of its mass as glycogen, barely enough to be used by the muscle as its own energy reserve.

Normally, blood glucose concentration is regulated by two hormones, insulin and glucagon, secreted by the pancreas. Insulin is released in a bimodal fashion from the pancreas in direct response to a rise in blood glucose level and, to a lesser extent, to a rise in the blood level of free fatty acids and amino acids. Insulin promotes transport of these nutrients into the cells to be utilized for energy, to be stored as glycogen or triglycerides, or to be synthesized into more complex compounds such as proteins.

Some individuals develop diabetes mellitus, and do not secrete insulin in sufficient quantities to properly regulate blood glucose. Lack of insulin inhibits the cell membrane transport of nutrients such as glucose, fatty acids, and amino acids into the cells, forcing the cells to use other compounds for energy and cell growth. Diabetics exhibit a decreased utilization of those nutrients by the cells, resulting in a marked increase in blood glucose concentration, an increase in triglyceride mobilization from the adipose tissue resulting in a marked increase in blood fatty acid and cholesterol concentrations, and a marked loss of protein on a cellular level. Most of the severe end-organ complications which result from diabetes are due to the cellular wasting which occurs secondary to abnormal amino acid uptake and protein wasting. Abnormal fatty acid metabolism results in elevated levels of blood concentrations of low-density lipoproteins (LDL), cholesterol, and free fatty acids, all leading to accelerated atherosclerosis and obstructive vascular disease. Those with diabetes are also prone to ketosis, and develop dehydration, acidosis, and electrolyte imbalance under stress. In some forms of the disease, insulin injections may be required, and other long-term complications such as retinopathy, blindness and kidney disease commonly occur.

The pancreas also secretes glucagon, a hormone which has cellular functions that are diametrically opposed to those of insulin. Glucagon stimulates the liver to release large amounts of glucose from glycogen when the blood glucose concentration falls below 90 mg/dl. This system of insulin inhibition and glycogen release prevents glucose concentrations from falling dangerously low.

In short, glucose is regulated within a narrow range between 80 and 90 mg/dl during fasting, with a rise toward 140 mg/dl following a high carbohydrate meal. The liver functions as a reservoir and buffer, so that glucose is available to the brain during meals and during periods of prolonged fast.

Type I diabetics have an absolute deficiency in insulin synthesis by the beta cells of the pancreas, and have the most severe clinical course if not aggressively managed with nutrition and insulin therapy. These individuals are ketosis prone and may develop a severe metabolic acidosis. Wide swings in blood glucose commonly occur with a high incidence of symptomatic hypoglycemia following insulin therapy. End organ dysfunction is common due to accelerated atherosclerosis, cellular protein wasting, and small vessel disease.

Type II diabetics release insulin from the pancreas in a blunted fashion following the intake of food. Blood insulin levels do not rise sufficiently to prevent hyperglycemia. In addition, peripheral tissues of type II diabetics may possess a smaller number of membrane tissue receptors and possibly a down regulation of those receptors. Ketoacidosis is uncommon. However, hyperglycemia and hyperosmolar conditions may occur, leading to coma and death. Insulin therapy may or may not be required to maintain normal glycemia levels. Other therapies include weight loss, diet, and oral hypoglycemic agents which stimulate the pancreas to release larger quantities of insulin.

There is no doubt that long term tight glucose control is able to significantly reduce the incidence of end organ complications. Control of blood glucose concentration in diabetic individuals by QID insulin injections has, of course, been done for many years. This type of treatment does have a number of serious drawbacks, however. One or more needle sticks of the finger must be performed on a daily basis to obtain blood for glucose assay. Many patients suffer anxiety and discomfort when subjected to finger pricking. After the blood sample is obtained, the sample must be exposed to a surface coated with chemical agents and enzymes that produce a color change corresponding to glucose concentration. The patient or medical practitioner performing the assay must interpret the color change accurately, and inject a dose of insulin based on the glucose level. Many individuals experience anxiety and discomfort when facing injections, and resist them. Some individuals may have no one to administer the required injections, but have difficulty injecting themselves. Dosage can also be problematic. Color change can be misinterpreted, and it is not unusual for patients to miss an injection, or to be off schedule. Syringes, which these days tend to be disposable, contribute to the growing problem of hazardous medical waste.

Some of these problems have been partially dealt with in the past, but none of the past attempts at dealing with these problems has been entirely satisfactory. Non-invasive optical techniques for measuring blood glucose have been developed, but these techniques do not solve the problems associated with administering insulin injections where required. Non-invasive optical techniques for measuring blood glucose are prone to error because the interface between the sensor and the tissue changes constantly with manipulation and contact pressure. Skin and extremity blood flow also varies considerably with cardiac output, body temperature and level of activity. These non-invasive optical techniques typically use a source of infrared (IR) radiation and a detector to measure absorption, reflection, or some other parameter to derive information about blood glucose levels. The effective optical distance from the IR source and the detector changes with subcutaneous body fat and the variability in placing the sensor from day to day. In addition, non-invasive IR sensors measure blood glucose in a non-continuous manner, and are thereby limited to functioning as a glucose measuring device and not as a therapeutic device for the treatment of diabetes.

Implantable pumps for administering insulin are known, and it has even been proposed to automatically measure blood glucose and administer insulin as may be required using an implantable sensor and insulin pump. However, the latter system uses a sensor which performs chemical analysis of blood samples, and thus requires the introduction of chemical reagents into the patient's body. In addition, the reagents periodically need to be replenished, which imposes the requirement of including a port below the surface of the skin through which fresh reagents must be injected from time to time. Thus, this system does not completely eliminate the need for periodic injections. The refilling process presents the danger of leaking a highly concentrated insulin solution into the body, which can result in severe hypoglycemia. Moreover, commercially available implantable pumps have FDA approval only for the infusion of chemotherapy and Baclofen for the treatment of spastic leg disorders. Pumps implanted for the infusion of insulin are still considered experimental.

An implantable sensor using a semipermeable membrane and an enzyme coated surface and oxygen electrode has been studied for the continuous measurement of blood glucose. This sensor has significant drift and quickly fails due to host reaction and contamination of the membrane and enzyme surface. Needle-type amperometric glucose sensors implanted within the subcutaneous tissues and having an enzyme coated surface and an electrical output to an external processor are known, but loss of sensitivity and sensor drift occur upon implantation. This type of sensor, which is in the form of a thin wire, must be inserted through a hollow needle into the subcutaneous tissue and must be changed every three to four days due to enzyme depletion and membrane contamination.

There is therefore a need to control levels of blood constituents, such as glucose concentration, fatty acid concentration, and amino acid concentration, in patients with diabetes which does not require blood sampling, chemical test reagents or reagent injections, and which provides continuous monitoring of levels of blood constituents. The present invention meets that need by providing a sensor which is fully implantable and can be used in vivo, can be used continuously and over the long term, and which is reliable and safe.

The present invention provides the ability to achieve close, continuous monitoring and control of insulin, which provides a clinical and therapeutic breakthrough.

SUMMARY OF THE INVENTION

The present invention is an implantable device for sensing in vivo the level of at least one blood constituent in mammalian vascular tissue, and comprises at least one source of radiation from infrared through visible light, arranged to direct said radiation at said tissue, said radiation being affected by interaction with said tissue, and a plurality of detectors, each having associated with it a filter transparent to a discrete narrow band of radiation, each detector providing an output signal representative of detected radiation in said narrow band, the detectors being located with respect to the tissue to receive radiation affected by said tissue.

In another of its aspects, the present invention includes a device for both measuring and controlling the level of a blood constituent in a mammal, and comprises an implantable infrared source and sensor module for directing infrared radiation through vascular tissue and for sensing the infrared radiation after it has passed through the tissue and generating an output signal representative of the sensed infrared radiation, a processor module responsive to the output signal from the infrared source and sensor module for performing spectral analysis of the output signal and deriving therefrom a control signal representative of the level of the blood constituent, and an insulin pump for dispensing doses of insulin in response to the control signal.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DESCRIPTION OF THE INVENTION

Figure 1:
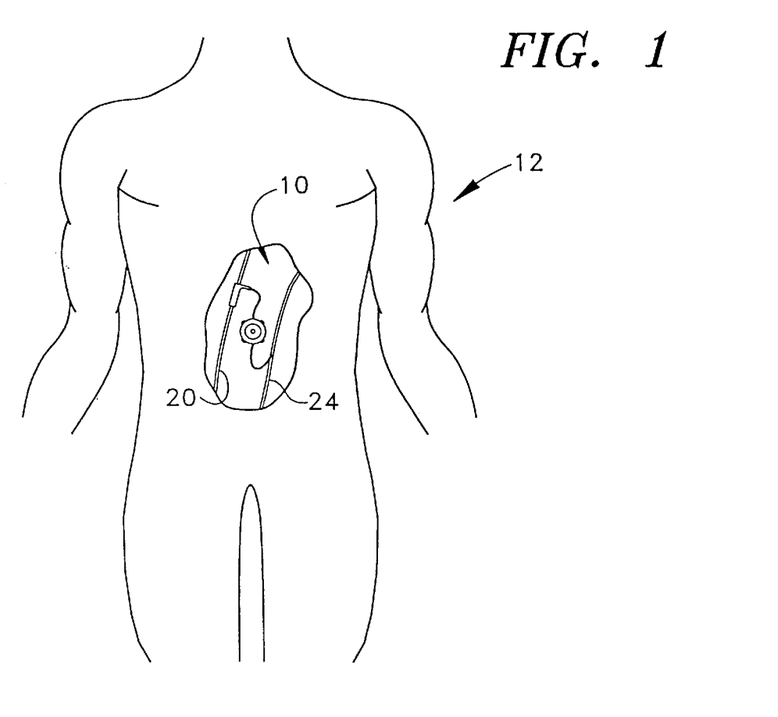
FIG. 1 illustrates an implantable glucose sensor according to one embodiment of the invention as it might be implanted in a human patient, shown in conjunction with an implantable insulin pump, with the sensor array arranged to monitor blood flow through a blood vessel.

Referring now to the drawings, wherein like numerals indicate like elements, there is shown in FIG. 1 a representation of an implantable blood glucose monitoring and control system 10 comprising a sensor and an insulin pump, as it might be surgically implanted in a patient 12. It should be understood that FIG. 1 is not intended to be anatomically accurate in every detail; rather, it is intended to represent generally how the system 10 would be implanted. Moreover, it should also be understood that, while for convenience the present invention is illustrated and described in reference to monitoring and control of blood glucose, the invention is not so limited, and encompasses the monitoring and control of other blood constituents such as, by way of example and not by way of limitation, fatty acid or amino acid concentration.

Figure 2:
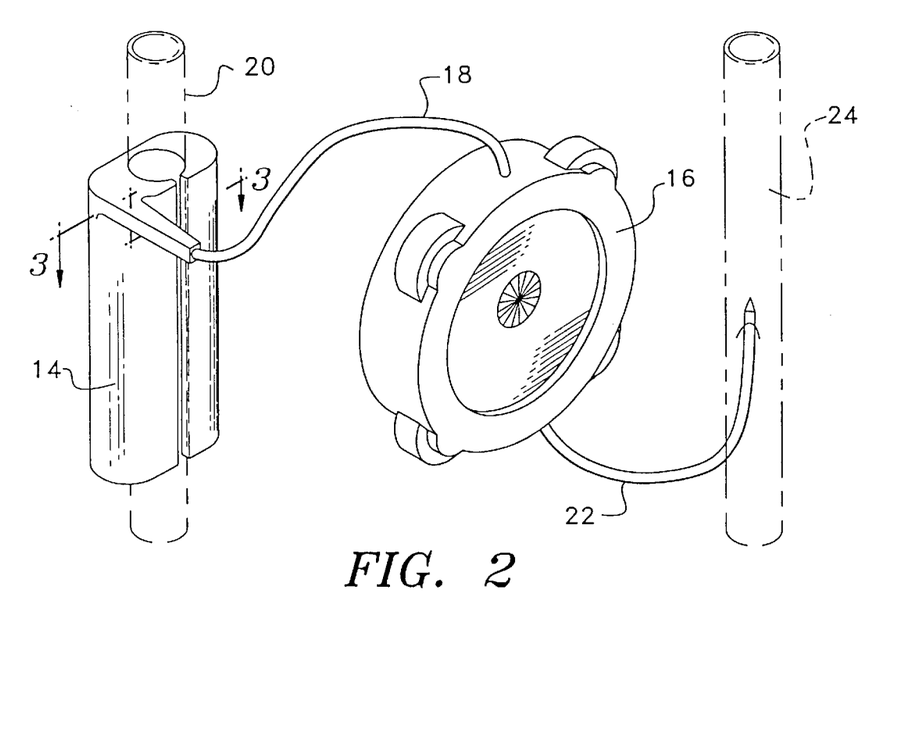
FIG. 2 is an enlarged view of the sensor of FIG. 1, showing the sensor in conjunction with an implantable insulin pump and processor module containing associated processing and control electronics.

As best seen in FIG. 2, system 10 comprises a sensor assembly 14 connected to a processor/pump module 16 via a signal cable 18. Sensor assembly 14, described in greater detail below, has an opening which enables it to be arranged to substantially surround a blood vessel 20. Processor/pump module 16 is illustrated as dispensing insulin via a tube 22 into a second blood vessel such as a vein 24, which may be the portal vein for direct transport to the liver. Alternatively, processor/pump module dispenses insulin via a non-thrombogenic multilumen catheter including a one-way valve, directly into the peritoneal space adjacent the hilum of the liver. Insulin will be rapidly absorbed into the portal venous system and transported to the liver. While the processor/pump module 16 is illustrated as implanted within a patient's body, the pump portion of processor/pump module 16 may also be an external device, worn or otherwise carried by the patient, without departing from the present invention. Where an external pump is used, insulin may be delivered percutaneously into an infusaport implanted under the patient's skin for final transport to the peritoneal cavity or portal vein. Alternatively, insulin may also be delivered by an external device with a needle placed chronically within the patient's subcutaneous tissues. Moreover, when an external pump is used, the processor portion of processor/pump module 16 requires a data telemetry portion in order to telemeter command signals to the external pump. Insulin reservoirs and pumps, telemetry devices, and infusaports are all known per se, and therefore need not be described here in any great detail.

Processor/pump module 16 contains a conventional insulin reservoir and pump. In addition to an insulin reservoir and pump, processor/pump module 16 contains an electronic microprocessor and associated electronic circuitry for generating signals to and processing signals from sensor assembly 14 and for generating control signals to the insulin pump itself. Processor/pump module 16 further includes a long-life battery to power the electronic circuitry, the sensor assembly 14 and the insulin pump.

Figures 3, 4:
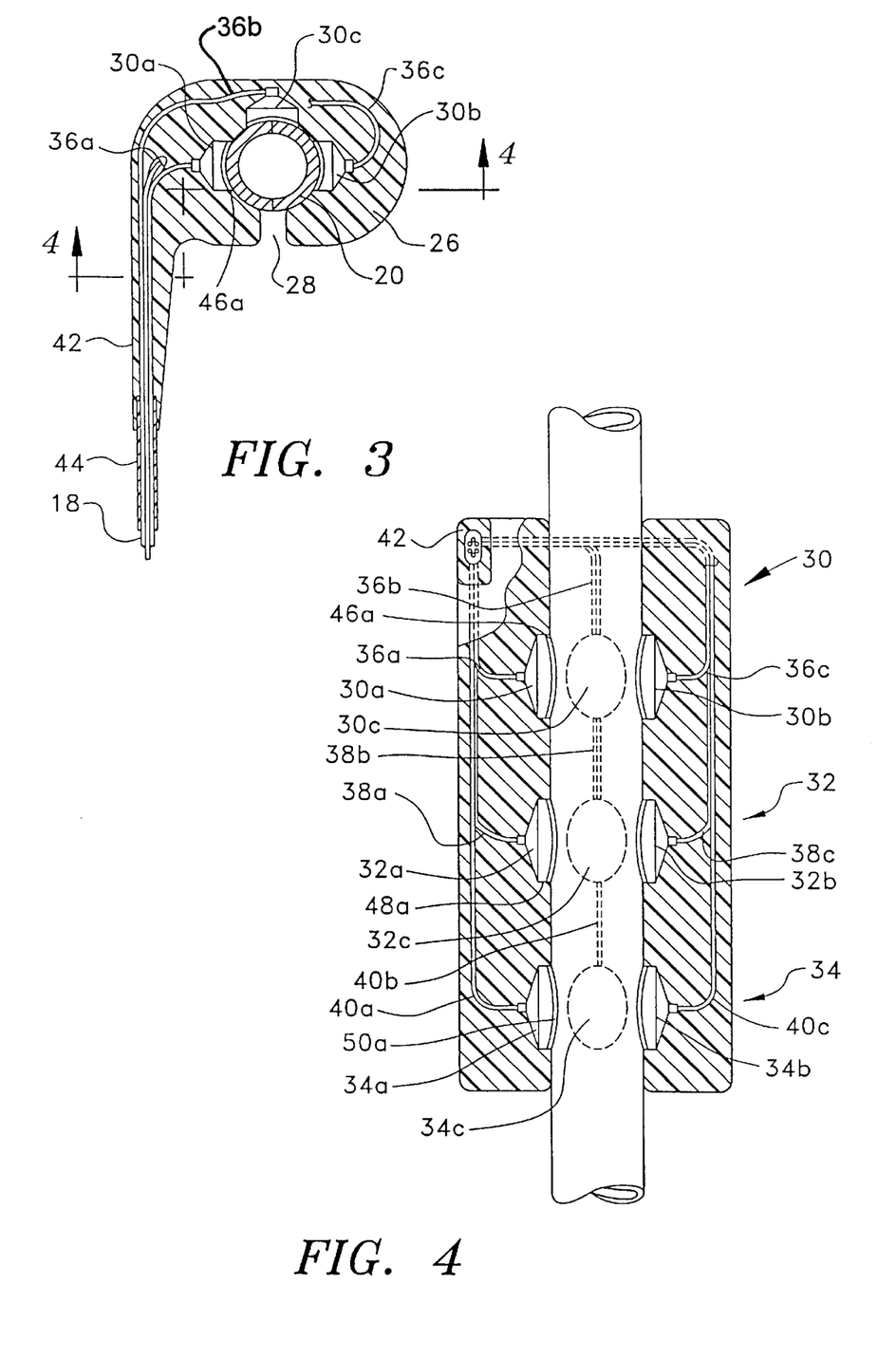
FIG. 3 is a transverse sectional view through the sensor shown in FIG. 2, taken along the lines 3—3 in FIG. 2, showing the distribution of individual photocells.
FIG. 4 is a longitudinal sectional view through the sensor, taken along the lines 4—4 in FIG. 3.
Figure 5:
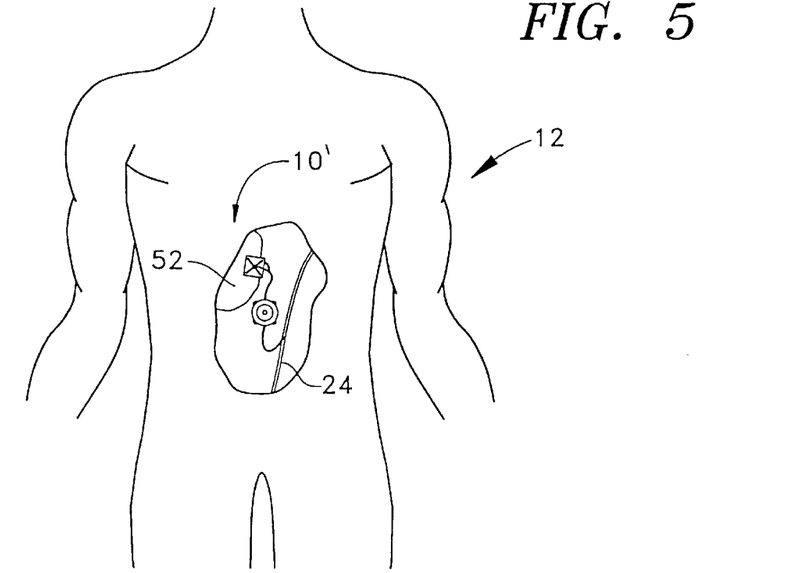
FIG. 5 illustrates an implantable glucose sensor according to an alternate embodiment of the invention as it might be implanted in a human patient, with a sensor array arranged to monitor blood flow through a vascular membrane such as the visceral peritoneum.

Sensor assembly 14 is illustrated in greater detail in FIGS. 3 and 4. Sensor assembly 14 has a body portion 26 which is generally C-shaped in transverse cross-section. Thus, body portion 26 has a longitudinal channel which runs through body portion 26, and a longitudinal gap 28 which communicates with the longitudinal channel. Body portion 26 is preferably fabricated from a semi-rigid material such as titanium or epoxy, which is easily worked and biocompatible for long-term implantation. The shape and semi-rigid material of sensor assembly 14 enable it to be placed closely around vessel 20 and place optical sources and individual optical detectors in optimum position with respect to vessel 20. The distance between the optical sources and the optical detectors can thus be made small and as close to constant as possible, for optimum signal acquisition.

In the embodiment of sensor 14 illustrated in FIGS. 3 and 4, the optical sources and optical detectors may be infrared (IR) sources and IR detectors, although radiation from infrared through the visible spectrum may be employed without departing from the invention. In the figures, individual IR sources and individual IR detectors are grouped together in three groups, or arrays, 30, 32, and 34. Each array comprises an IR source (30a, 32a, and 34a, respectively) and two IR detectors (30b, 30c; 32b, 32c; and 34b, 34c, respectively). The individual IR sources 30a, 32a, and 34a may be miniature infrared diodes located, in the illustrated embodiment, on one side of vessel 20. IR sources 30a, 32a, and 34a are driven by signals generated in the processor/pump module 16 and transmitted to IR sources 30a, 32a, and 34a via conductors 36a, 38a, and 40a, respectively. Similarly, output signals from individual detectors 30b, 30c; 32b, 32c; and 34b, 34c are transmitted to processor/pump module 16 via conductors 36b, 36c; 38b, 38c; and 40b, 40c, respectively. Conductors 36, 38, and 40 collectively are dressed together to form signal cable 18, which couples sensor array 14 to processor/pump module 16. Cable 18 exits body portion through an extension portion 40, which serves to support cable 18 and minimize the chance of breakage of conductors 36, 38, and 40 from flexing or being subjected to sharp bends. If desired, cable 18 may exit extension portion 42 through a strain relief sleeve 44, to further protect cable 18.

Each IR source 30a, 32a, and 34a has associated with it an optical filter 46a, 48a, and 50a, respectively. Each filter transmits a different discrete narrow band of radiation. In similar fashion, each detector 30b, 30c; 32b, 32c; and 34b, 34c has associated with it an optical filter 46b, 46c; 48b, 48c; and 50b, 50c, respectively. In this manner, each optical source and the detectors associated with it in a given array 30, 32, or 34 operates in only a discrete narrow band.

With this embodiment, detectors 30c, 32c, and 34c are arranged diametrically opposite IR sources 30a, 32s, and 34a, respectively, to detect light transmitted from the associated source through the blood vessel 20. The angle between the sources and the detectors is thus 180°. (These detectors could also be used to determine reflected light, since light that is not transmitted may, for purposes of the invention, be assumed to have been reflected. By determining the amount of light transmitted, and subtracting it from the amount of light emitted from the source, the amount of light reflected can be calculated.) Detectors 30*b*, 32*b,* and 34*b* are arranged at an angle less than 180° from the associate sources, and are located to detect IR radiation either reflected or scattered from vessel 20.

It is important to note that, although this embodiment of the invention is described using three arrays of IR sources and associated detectors, that precise configuration is not crucial to the invention. The invention may be implemented, for example, using a single IR source and multiple detectors for detecting reflected, scattered, and transmitted IR radiation. In such an embodiment, the IR source would not have a narrow band filter associated with it, but would emit broadband IR. Each detector, however, would have a narrow band filter associated with it, so that it would respond only to a preselected wavelength.

Conductors 36, collectively, 38, collectively, and 40, collectively, can be either electrical conductors or optical fibers. That is, the IR sources and the IR detectors may be located either within sensor assembly 14 itself, in which case the conductors are electrical conductors and carry electrical signals between processor/pump module 16 and sensor assembly 14, or within processor/pump module 16, in which case the conductors are optical fibers and carry infrared radiation between processor/pump module 16 and sensor assembly 14.

It will be appreciated that IR radiation generated by IR sources 30*a,* 32*a,* and 34*a* is directed through the walls of vessel 20, and thus the blood flowing in the vessel, to detectors 30*b,* 30*c;* 32*b,* 32*c;* and 34*b,* 34*c* located across from and at right angles to the IR sources. The IR radiation detected by the several detectors is, of course, affected by its interaction with vessel 20 and the blood flowing therethrough. Consequently, by analyzing the output signals from the several detectors, it is possible to derive information about the levels of glucose, fatty acids, and amino acids in the blood flowing through vessel 20. Preferably, although not necessarily, selected sensor/detector pairs are used for different measurement techniques. For example, pair 30*a,* 30*b* could be used to measure infrared transmittance, and pair 30*a,* 30*c* to measure infrared scattering. That is, the output signals from the several detectors can be processed differently to obtain different characteristics of the blood being measured. Using Fourier transform infrared spectroscopy (FTIR) analysis, it is possible to correlate the sensor output data with blood glucose levels, blood fatty acid levels, and blood amino acid levels.

In contrast to prior electro-chemical glucose sensors, sensor array 14 does need require direct contact with blood, does not need to be replenished with test reagents, and can operate indefinitely.

Figure 6:
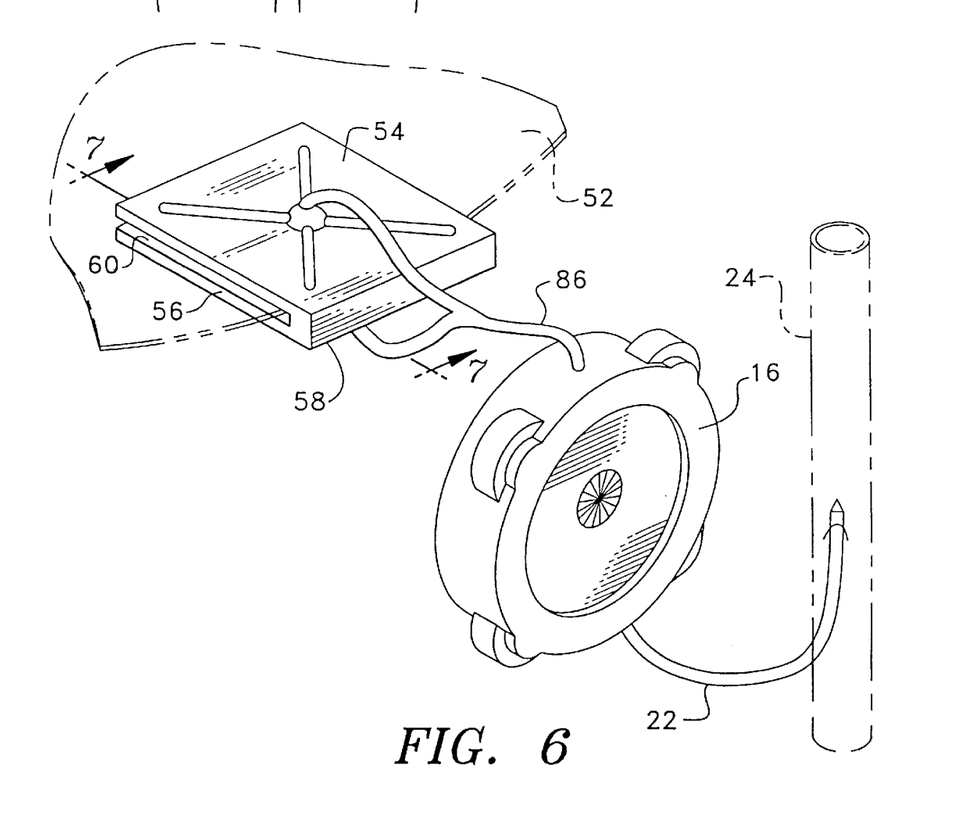
FIG. 6 is an enlarged view of the embodiment of the sensor of FIG. 5, showing the sensor in conjunction with an implantable insulin pump and processor module containing associated processing and control electronics.
Figure 7:
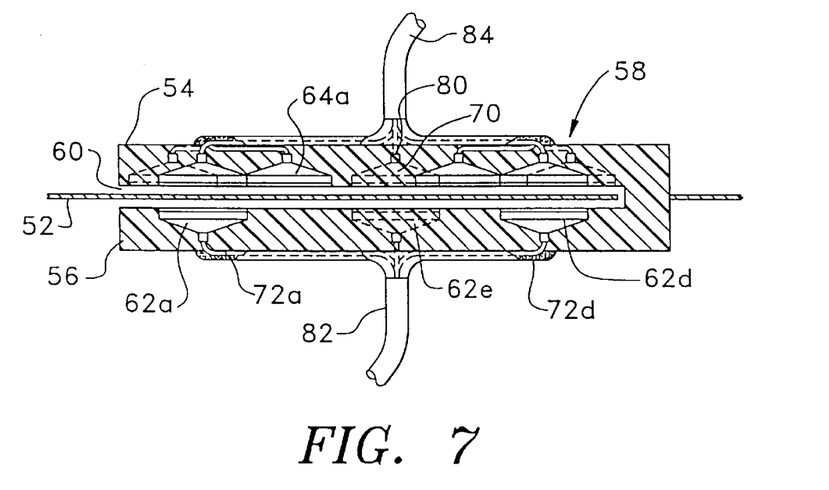
FIG. 7 is a sectional view through the sensor shown in FIG. 6, taken along the lines 7—7 in FIG. 6.
Figure 8:
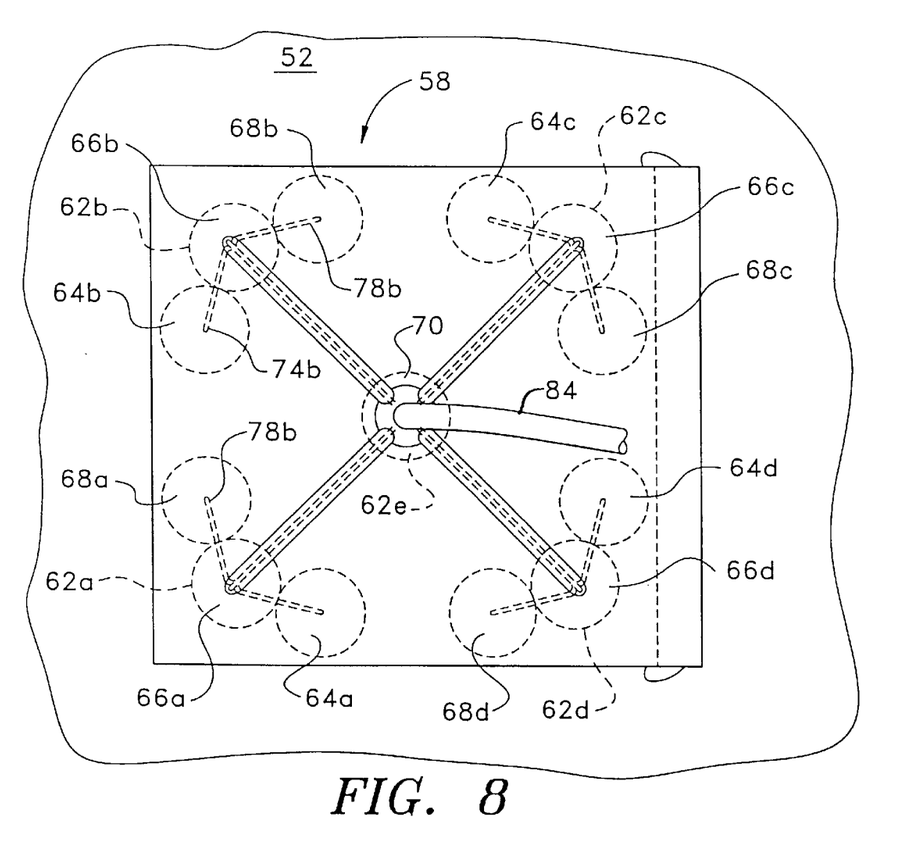
FIG. 8 is a top plan view of the sensor shown in FIG. 6, showing the distribution of individual photocells.

An alternative form of device 10' according to the present invention is illustrated in FIGS. 5 through 8. In alternative form 10', the device monitors blood flowing through highly vascular membrane, such as a portion of the visceral peritoneum 52. Visceral peritoneum is an ideal tissue for measurement due to its high vascularity, translucency, constant temperature, and brisk blood flow. As best seen in FIGS. 6 and 7, a portion of a vascular membrane such as the visceral peritoneum 52 (shown in phantom in FIG. 6) is sandwiched between two halves 54 and 56 of an alternate form 58 of sensor assembly. Halves 54 and 56 are essentially mirror images of each other, and define a gap 60 between them, which receives the peritoneal tissue. Sensor assembly 58 is preferably molded from the same type of material as used to fabricate sensor assembly 14, as already described. The shape and semi-rigid material of sensor assembly 58 enable it to be clamped snugly around peritoneal tissue 52 and to place individual IR sources 62*a* though 62*de* and individual IR detectors 64*a* through 64*d,* 66*a* through 66*d,* 68*a* through 68*d,* and 70, in optimum position with respect to tissue 52.

One half of sensor assembly 58, such as half 56 for example, contains the individual IR sources 62*a* through 62*e,* while the other half, such as half 54, for example, contains the individual detectors 64 collectively, 66 collectively, 68 collectively, and 70. The detectors are grouped together in groups of three, for example, such as 64*a,* 66*a,* and 68*a,* and are located opposite a source, such as 62*a.* Only a single detector 70 is shown located opposite source 62*e,* although a group of detectors could also be located opposite source 62*e.*

IR sources 62, collectively, are driven by signals generated in the processor/pump module 16 and transmitted to IR sources 62*a* through 62*e* via conductors 72*a* through 72*e,* respectively. Similarly, output signals from individual detectors 64*a* through 64*e,* 66*a* through 66*e,* 68*a* through 68*e,* and 70 are transmitted to processor/pump module 16 via conductors 74*a* through 74*e,* 76*a* through 76*e,* 78*a* through 78*e,* and 80, respectively. Conductors 72, collectively, are dressed together to form a signal cable 82, while conductors 74 collectively, 76 collectively, 78 collectively, and 80 are dressed together to form a signal cable 84. Cables 82 and 84 are merged together into a single signal cable 86 (see FIG. 6), which connects sensor assembly 58 to processor/pump module 16.

As with conductors 36, 38, and 40, conductors 72, 74, 76, 78, collectively, and 80 can be either electrical conductors or optical fibers. That is, the IR sources 62, collectively, and the IR detectors 64, 66, 68, collectively, and 70 may be located either within sensor assembly 58 itself, in which case the conductors are electrical conductors and carry electrical signals between processor/pump module 16 and sensor assembly 58, or within processor/pump module 16, in which case the conductors are optical fibers and carry infrared radiation between processor/pump module 16 and sensor assembly 58.

IR radiation generated by IR sources 62, collectively, is directed through peritoneal tissue 52, and thus the blood flowing through the tissue, to detectors 64, 66, 68, collectively, and 70 located across from the IR sources. As in the previous embodiment, each source or detector may have associated with it a narrow band filter, so that each optical source and the detectors associated with it in a given array operate in only a discrete narrow band of IR radiation. The IR radiation detected by detectors 64, 66, 68, collectively, and 70 is, of course, affected by its interaction with tissue 52 and the blood flowing therethrough. Consequently, by analyzing the output signals from the detectors, it is possible to derive information about the blood flowing through tissue 52. Preferably, although not necessarily, selected sensor/detector pairs are used for different measurement techniques, such as, for example, infrared transmittance, infrared reflectance, and infrared scattering. Thus, the output signals from the individual detectors can be processed differently to obtain different characteristics of the blood being measured. Using Fourier transform infrared spectroscopy (FTIR) analysis, it is possible to correlate the sensor output data with blood glucose levels, blood fatty acid levels, and/or blood amino acid levels.

Figure 9:
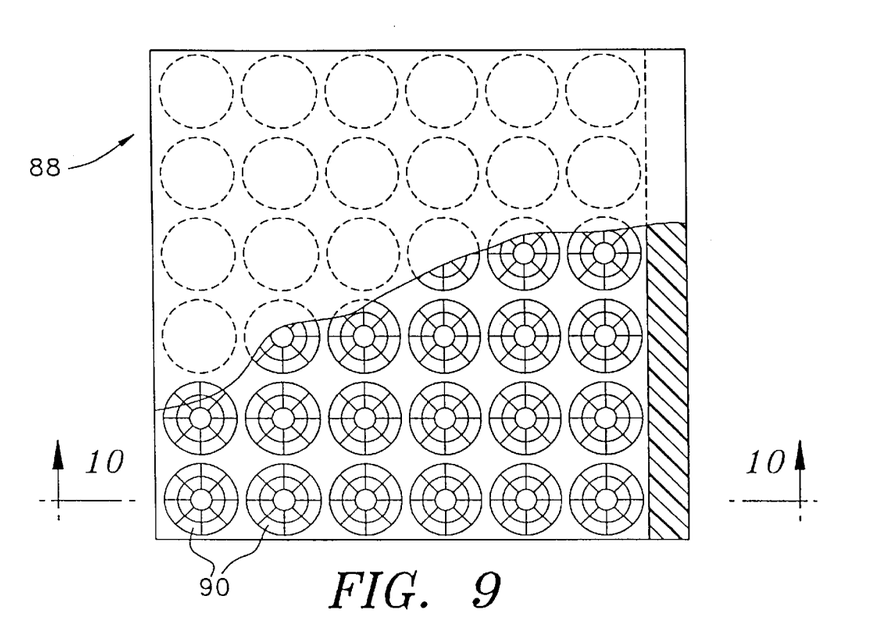
FIG. 9 illustrates a third embodiment of the invention, partially broken away, showing an arrangement of individual photocells in a rectangular array.
Figure 10:
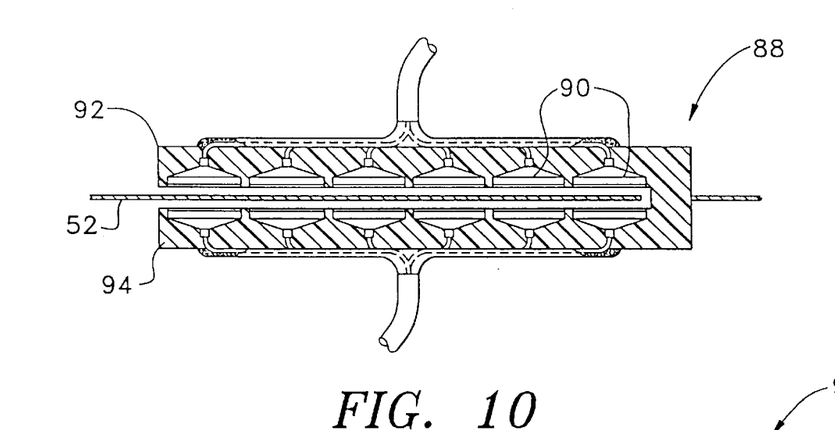
FIG. 10 is a sectional view of the sensor shown in FIG. 9, taken along the lines 10—10 in FIG. 9.

A third embodiment 88 of sensor assembly is illustrated in FIGS. 9 and 10. In those figures, sensor assembly 88 comprises a generally rectangular array of source/detectors 90 disposed on opposite halves 92 and 94 of the sensor assembly, with each half being on opposite sides of the visceral peritoneum 52. Source/detectors 90 are preferably, although not necessarily, arranged opposite one another on respective halves 92 and 94, so that the array on one half is substantially in registry with the array on the other half.

Figure 11:
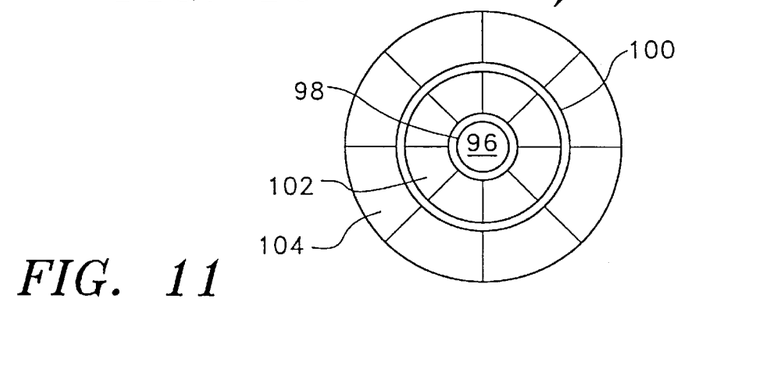
FIG. 11 is an enlarged plan view of an individual photocell from the array shown in FIG. 9.

An individual source/detector 90 is illustrated in more detail in FIG. 11. Source/detector 90 is generally circular, and at its center portion contains a source segment 96, from which infrared radiation is emitted. An inactive buffer ring 98 surrounds source segment 96. A second inactive buffer ring 100 is radially spaced from and surrounds buffer ring 98. Buffer rings 98 and 100 are inactive in the sense that they neither emit nor respond to IR radiation. The portion of source/detector 90 between buffer rings 98 and 100 is divided into a plurality of detector segments 102, each of which is associated with a narrow band filter so that it responds to a selected band of radiation. A linearly-variable filter can be used, for example. In this manner, each detector segment 102 operates in only a discrete narrow band. A second plurality of detector segments 104 is located radially outward of buffer ring 100, each of which is also associated with a narrow band filter so that it, too, responds to a selected band of radiation.

It will be appreciated that a single source/detector 90 can operate to measure both reflected and scattered IR, or a single pair of source/detectors 90 can operate to measure reflected, scattered, and transmitted light over a plurality of discrete radiation bands.

Figure 12:
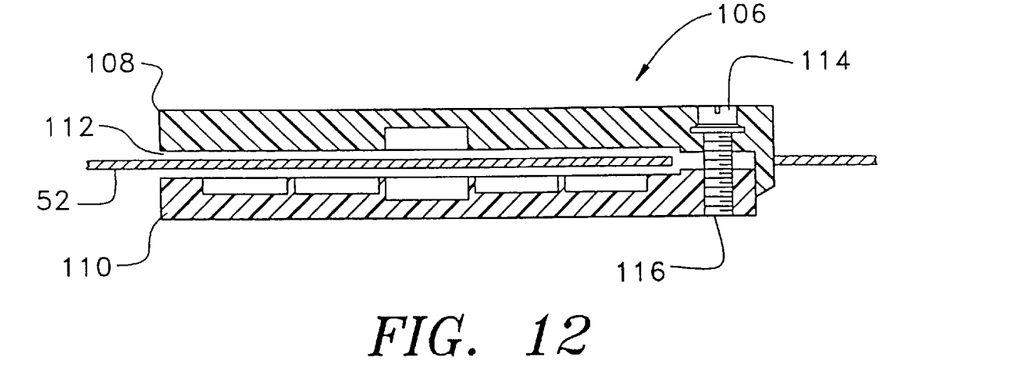
FIG. 12 is a fourth embodiment of the invention, in cross-sectional view.

FIG. 12 illustrates an embodiment 106 of a sensor assembly similar to those shown in FIGS. 7 and 10, except that the two halves 108 and 110 are not spaced apart by a fixed distance, as are the halves of the detectors in FIGS. 7 and 10. Instead, the halves 108 and 110 are movable toward and away from each other, and the gap 112 may be adjusted by means of adjusting screws 114. Preferably, the head portion of screw 114 is made captive, but freely rotatable, in one half, such as half 108. The shank portion of the screw is received in a threaded bore 116 in the opposite half. Thus, by rotating screw 114, the width of the gap 112 between halves 108 and 110 can be easily adjusted for optimum spacing of the individual sources and detectors relative to the visceral peritoneum 52.

Naturally, it should be understood that, although embodiments using different groupings of sources and detectors have been described, the invention is not in any way limited to a specific number of source/detector groupings, nor is it absolutely necessary that the sources and detectors be arranged in specific configurations.

As already noted, processor/pump module 16 contains an electronic microprocessor and associated electronic circuitry for generating signals to and processing signals from sensor assembly 14 and for generating control signals to the insulin pump itself. The microprocessor is preferably programmed to execute algorithms to perform multispectral correlation, and matched digital bandpass filtering to remove low frequency bias and high frequency noise. Such algorithms are well-known to those skilled in the art, and need not be described in detail. Moreover, the invention is not limited to any specific algorithm; rather, any algorithms suitable for performing the desired multispectral correlation and filtering functions may be used without departing from the invention. It should also be noted that, while the present invention provides accurate glucose level measurements, accurate measurement is not crucial to the control of the insulin pump 16. In a manner similar to the way a house thermostat operates, the pump 16 can be controlled to release a fixed quantity of insulin until the glucose levels falls below a preselected level. Thus, any algorithm capable of such control is within the scope of the invention. The algorithm may also control insulin pump 16 to release a glucagon bolus, such as 1 mg of glucagon, when blood glucose levels trend below 60 mg/dl.

Processor/pump module 16 may also contain a telemetry transmitter to transmit sensor data to an external processor and external insulin pump. Insulin can be injected subcutaneously or into a subcutaneous infusaport for delivery into the peritoneal cavity or into a portal vein.

Processor/pump module 16 may also consist of a telemetry receiver for external calibration. If recalibration is necessary, the system 10 may be recalibrated externally by comparison to a weekly or monthly finger stick blood glucose measurement, such as, for example, using calorimetric assay of a glucose oxidase/hydrogen peroxide reaction using standard techniques. The absolute glucose amount from the external calibration measurement can then be telemetered to the processor for calibration.

The present invention may be embodied in other specific forms without departing from the spirit or essential attributes thereof and, accordingly, reference should be made to the appended claims, rather than to the foregoing specification, as indicating the scope of the invention.

We claim:

1. An implantable device for sensing in vivo the level of at least one blood constituent in mammalian vascular tissue, comprising:

at least one implantable source of radiation from infrared through visible light, arranged to direct said radiation at said tissue, said radiation being affected directly by interaction with said tissue, and a plurality of implantable detectors, each having associated with it a filter transparent to a discrete narrow band of radiation, each detector providing an output signal representative of detected radiation in said narrow band, the detectors being located with respect to the tissue to receive said radiation affected directly by interaction with said tissue.

2. An implantable device for sensing in vivo the level of at least one blood constituent in mammalian vascular tissue according to claim 1, further comprising a channel having an internal circumference around which are arranged said source and said detectors, said channel being dimensioned to receive a blood vessel therein and to locate said vessel in proximity to said source and detectors.

3. An implantable device for sensing in vivo the level of at least one blood constituent in mammalian vascular tissue according to claim 1, further comprising a first half and a second half, one half supporting said at least one source and the other half supporting at least one of said plurality of detectors, said halves being spaced apart and defining a gap therebetween for receiving said vascular tissue therein and locating said tissue in proximity to said source and detectors.

4. An implantable device for sensing in vivo the level of at least one blood constituent in mammalian vascular tissue according to claim 3, further comprising said halves being separate from one another and movable reciprocally toward and away from each other for varying the size of said gap.

5. An implantable device for sensing in vivo the level of at least one blood constituent in mammalian vascular tissue according to claim 4, further comprising an adjustable fastener for adjustably fastening said halves together and for adjustably varying the size of said gap.

6. An implantable device for sensing in vivo the level of at least one blood constituent in mammalian vascular tissue according to claim 5, wherein the adjustable fastener comprises a rotatable screw in one of said halves and a threaded bore receiving said screw in the other of said halves.

7. An implantable device for sensing in vivo the level of at least one blood constituent in mammalian vascular tissue according to claim 1, wherein said at least one source and said plurality of detectors are arranged in a linear array, at least one of said plurality of detectors being located opposite said source and spaced therefrom by a distance sufficient to receive said tissue between said source and said detector.

8. An implantable device for sensing in vivo the level of at least one blood constituent in mammalian vascular tissue according to claim 1, wherein said at least one source and said plurality of detectors are arranged in a planar array, at least one of said plurality of detectors being located opposite said source and spaced therefrom by a distance sufficient to receive said tissue between said source and said detector.

9. An implantable device for sensing in vivo the level of at least one blood constituent in mammalian vascular tissue according to claim 1, wherein at least one detector of said plurality of detectors is located opposite said source and at least one detector of said plurality of detectors is located next to said source.

10. An implantable device for sensing in vivo the level of at least one blood constituent in mammalian vascular tissue according to claim 1, wherein at least one of said plurality of detectors is located to detect radiation scattered by said tissue.

11. An implantable device for sensing in vivo the level of at least one blood constituent in mammalian vascular tissue according to claim 1, wherein at least one of said plurality of detectors is located to detect radiation transmitted through said tissue.

12. An implantable device for sensing in vivo the level of at least one blood constituent in mammalian vascular tissue according to claim 1, wherein at least one of said plurality of detectors is located to detect radiation reflected by said tissue.

13. An implantable device for sensing in vivo the level of at least one blood constituent in mammalian vascular tissue according to claim 1, wherein at least one of said plurality of detectors is located to detect radiation scattered by said tissue and at least one of said plurality of detectors is located to detect radiation transmitted through said tissue.

14. An implantable device for sensing in vivo the level of at least one blood constituent in mammalian vascular tissue according to claim 1, wherein at least one of said plurality of detectors is located to detect radiation scattered by said tissue, at least one of said plurality of detectors is located to detect radiation transmitted by said tissue, and at least one of said plurality of detectors is arranged to detect radiation reflected by said tissue.

15. An implantable device for sensing in vivo the level of at least one blood constituent in mammalian vascular tissue according to claim 1, wherein at least one optical fiber is used in conjunction with at least a selected one of said source and detectors for conveying said radiation between said selected one of said source and detectors and said tissue.

16. A device for measuring and controlling the level of blood glucose in a mammal, comprising:
   an implantable infrared source and sensor module for directing infrared radiation through vascular tissue and for sensing the infrared radiation after it has interacted directly with the tissue and generating an output signal representative of the direct interaction of infrared radiation with the tissue,
   a processor module responsive to the output signal from the infrared source and sensor module for performing spectral analysis of the output signal and deriving therefrom a control signal related to the level of said blood glucose, and
   an insulin pump for dispensing doses of insulin in response to the control signal.

17. A device for measuring and controlling the level of blood glucose in a mammal according to claim 16, wherein the insulin pump is external to the body of the mammal.

18. A device for measuring and controlling the level of blood glucose in a mammal according to claim 16, wherein the insulin pump is implantable within the body of the mammal.

19. A device for measuring and controlling the level of blood glucose in a mammal according to claim 16, wherein the source and sensor module comprises at least one source of radiation from infrared through visible light, arranged to direct said radiation at said tissue, said radiation being affected by interaction with said tissue, and a plurality of detectors, each having associated with it a filter transparent to a discrete narrow band of radiation, each detector providing an output signal representative of detected radiation in said narrow band, the detectors being located with respect to the tissue to receive radiation from said source affected by said tissue.

20. A device for measuring and controlling the level of a blood constituent in a mammal, comprising
   an implantable infrared source and sensor module for directing infrared radiation through vascular tissue and for sensing the infrared radiation after it has interacted directly with the tissue and generating an output signal representative of the direct interaction of infrared radiation with the tissue;
   a processor module responsive to the output signal from the infrared source and sensor module for performing spectral analysis of the output signal and deriving therefrom a control signal related to the level of said blood constituent; and
   a pump for dispensing doses of medication in response to the control signal.

* * * * *